(12) United States Patent
Koman et al.

(10) Patent No.: US 6,180,364 B1
(45) Date of Patent: Jan. 30, 2001

(54) PROTEIN CALLED EPIL/PLACENTIN, PROCESS FOR THE PREPARATION OF THIS PROTEIN AND PHARMACEUTICAL COMPOSITION CONTAINING SUCH, DNA CODING FOR SAID PROTEIN

(76) Inventors: Ahmet Koman, 5 Grand Rue, 78240 Chambourcy; Dorine Chassin, 126 Boulevard de la Liberation, 94300 Vincennes; Dominique Bellet, 18 Rue Diderot, 92170 Vanves, all of (FR)

( * ) Notice: Under 35 U.S.C. 154(b), the term of this patent shall be extended for 0 days.

(21) Appl. No.: 09/174,465

(22) Filed: Oct. 19, 1998

Related U.S. Application Data

(62) Division of application No. 08/482,842, filed on Jun. 7, 1995, now Pat. No. 5,910,480.

(30) Foreign Application Priority Data

Jun. 13, 1994 (FR) .................................................. 94 07191

(51) Int. Cl.⁷ ........................... C12P 21/06; C07H 17/00; C07K 14/00
(52) U.S. Cl. .................. 435/69.1; 435/320.1; 435/252.3; 435/325; 536/23.1; 530/350
(58) Field of Search ................................ 435/69.1, 320.1, 435/252.3, 325; 536/23.1; 530/350

(56) References Cited

FOREIGN PATENT DOCUMENTS

273369 * 6/1970 (JP) .
48-030370 * 11/1974 (JP) .

OTHER PUBLICATIONS

"Active Preparation Form Human Placental Tissue", (Database Biosis–Abstract), vol. 5 pp. 120–122 (1969).*
"Amino Acid Composition of New Blood Substituted from the Placenta", Altunyan et al. (Chem. Abstracts), vol. 78, No. 22 (Jun. 4, 1973).*
French Preliminary Search Report; Date of completion of search: Feb. 6, 1995.*

* cited by examiner

*Primary Examiner*—Karen Cochrane Carlson
(74) *Attorney, Agent, or Firm*—Burns, Doane, Swecker & Mathis, L.L.P.

(57) ABSTRACT

The subject of the invention is a new protein called EPIL or placentin, its analogs showing EPIL/placentin-type activity, obtained by deletion and/or substitution. The invention also concerns a DNA molecule coding for a EPIL/placentin-type polypeptide. It finally concerns a pharmaceutical composition containing EPIL/placentin or a EPIL/placentin analog.

8 Claims, 4 Drawing Sheets

```
agt ctg gag ccc aga agg gac aca cca gca cag tct ggt agg cta cag cag caa gtc tct    60
Ser Leu Glu Pro Arg Arg Asp Thr Pro Ala Gln Ser Gly Arg Leu Gln Gln Gln Val Ser aaa gaa agg ctg aga aca ccc aga gga ttc agg tcc agg ATG GCC AGC CTG TTC           120
Lys Glu Arg Leu Arg Thr Pro Arg Gly Phe Arg Ser Arg Met Ala Ser Leu Phe CGG TCC TAT CTG CCA GCA ATC TGG CTG CTG AGC CAA CTC CTT AGA GAA AGC CTA GCA       180
Arg Ser Tyr Leu Pro Ala Ile Trp Leu Leu Ser Gln Leu Leu Arg Glu Ser Leu Ala GCA GAG CTG AGG GGA TGT GGT CCC CGA TTT GGA AAA CAC TTG CTG TCA TAT TGC CCC ATG   240
Ala Glu Leu Arg Gly Cys Gly Pro Arg Phe Gly Lys His Leu Leu Ser Tyr Cys Pro Met CCT GAG AAG ACA TTC ACC ACC CCA GGG TGG CTG CTG GAA TCT GGA CGT CCC AAA           300
Pro Glu Lys Thr Phe Thr Thr Thr Pro Gly Trp Leu Leu Glu Ser Gly Arg Pro Lys GAA ATG GTG TCA ACC TCC AAG AAC AAA GAT GGA CAA GCC TTA GGT ACG ACA TCA GAA TTC   360
Glu Met Val Ser Thr Ser Lys Asn Lys Asp Gly Gln Ala Leu Gly Thr Thr Ser Glu Phe
```

FIGURE 1A

```
ATT CCT AAT TTG TCA CCA GAG CTG AAG AAA CCA CTG TCT GAA GGG CAG CCA TCA TTG AAG    420
Ile Pro Asn Leu Ser Pro Glu Leu Lys Lys Pro Leu Ser Glu Gly Gln Pro Ser Leu Lys

AAA ATA ATA CTT TCC CGC AAA AAG AGA AGT GGA CGT CAC AGA TTT GAT CCA TTC TGT TGT    480
Lys Ile Ile Leu Ser Arg Lys Lys Arg Ser Gly Arg His Arg Phe Asp Pro Phe Cys Cys

GAA GTA ATT TGT GAC GAT GGA ACT TCA GTT AAA TTA TGT ACA tag tag agt aat cat gga    540
Glu Val Ile Cys Asp Asp Gly Thr Ser Val Lys Leu Cys Thr Xaa Xaa Ser Asn His Gly ctg gac atc tca tcc att ctc ata tgt att ctc aat gac aaa ttc act gat gcc caa tta    600
Leu Asp Ile Ser Ser Ile Leu Ile Cys Ile Leu Asn Asp Lys Phe Thr Asp Ala Gln Leu aat gat tgc tgt tta    615
Asn Asp Cys Cys Leu
```

FIGURE 1B

...5'aggtcagttctattttattcatctaagcaaaggacattaaaaattaccattatttttagtaagcataaaatagtattaca
ggaggaaagttaagaaaaaagaagtagaacaaccaaattcaaaacaagcaaagtgcagcacattgggagcaaagagggatatgag
agtgtgggtagggcaagtagggagactaaataagaactgagg gagaaagttcctgtaggtgggtgggaaaggggtgactgacac
cattgacgccaaagctgagtatagccctaagccaaataaatgcctgatgaaggcatgcagaaag Exon 1

1  CAGTCTGGAGCCCAGAAGGGACACACCAGCACACAGTCTGGTAGGCTACAGCAGCAAGTCTCTAAAGAAAGGCTGAGAACACCCAGAAC
   AGGAGAGTTCAGGTCCAGG

106 ATG GCC AGC CTG TTC CGG TCC TAT CTG CCA GCA ATC TGG CTG CTG CTG AGC  | CAA CTC CTT AGA
    Met Ala Ser Leu Phe Arg Ser Tyr Leu Pro Ala Ile Trp Leu Leu Leu Ser  | Gln Leu Leu Arg
    -17                                                             -1  | 1 B-chain 169 GAA AGC CTA GCA GCA GAG CTG AGG GGA TGT GGT CCC CGA TTT GGA AAA CAC TTG CTG TCA TAT TGC
    Glu Ser Leu Ala Ala Glu Leu Arg Gly Cys Gly Pro Arg Phe Gly Lys His Leu Leu Ser Tyr Cys
    5

235 CCC ATG CCT GAG AAG ACA TTC ACC ACC CCA GGA GGG TGG CTG|CTG GAA TCT GGA CGT CCC AAA
    Pro Met Pro Glu Lys Thr Phe Thr Thr Pro Gly Gly Trp Leu|Leu Glu Ser Gly Arg Pro Lys
    27                                                              C-peptide

FIGURE 2A

```
Intron 1  gtgagagccctggactaccaaacaatcagaatgagggctgaaaaaaca ...
          acatgaatgttttcctcacctttcattcctctcttttacttcacag Exon 2  302  AA ATG GTG TCA ACC TCC AAC AAC AAA GAT GGA CAA GCC TTA GGT ACG ACA TCA GAA TTC ATT CCT
         69  Glu Met Val Ser Thr Ser Asn Asn Lys Asp Gly Gln Ala Leu Gly Thr Thr Ser Glu Phe Ile Pro 367  AAT TTG TCA CCA GAG CTG AAG AAA CCA CTG TCT GAA GGG CAG CCA TCA TTG AAG AAA ATA ATA CTT|
         71  Asn Leu Ser Pro Glu Leu Lys Lys Pro Leu Ser Glu Gly Gln Pro Ser Leu Lys Lys Ile Ile Leu|

433  TCC CGC AAA AAG AGA AGT GGA CGT CAC AGA TTT GAT CCA TTC TGT TGT GAA GTA ATT TGT GAC GAT
         93  Ser Arg Lys Lys Arg Ser Gly Arg His Arg Phe Asp Pro Phe Cys Cys Glu Val Ile Cys Asp Asp
              A-chain 499  GGA ACT TCA GTT AAA TTA TGT AAA TTA TGT ACA TAG TAGAGTAATCATGACTGGACATTCTCATTCATTCTCATATGTATTCTCAAT
        115  Gly Thr Ser Val Lys Leu Cys Lys Leu Cys Thr ***

527  GACAAAATTCACTGATGCCCAATTAAATGATTGCTGTTT   3' ...
```

FIGURE 2B

SEQUENCE LISTING

```
<160> NUMBER OF SEQ ID NOS:  16

<210> SEQ ID NO 1
<211> LENGTH: 615
<212> TYPE: DNA
<213> ORGANISM: Unknown
<220> FEATURE:
<221> NAME/KEY: CDS
<222> LOCATION: (1)..(615)
<223> OTHER INFORMATION: Description of Unknown Organism:EPIL - Early
      Placenta Insulin-Like Peptide

<400> SEQUENCE: 1 agt ctg gag ccc aga agg gac aca cca gca cag tct ggt agg cta cag      48
Ser Leu Glu Pro Arg Arg Asp Thr Pro Ala Gln Ser Gly Arg Leu Gln
  1               5                  10                  15 cag caa gtc tct aaa gaa agg ctg aga aca ccc aga aca gga gag ttc      96
Gln Gln Val Ser Lys Glu Arg Leu Arg Thr Pro Arg Thr Gly Glu Phe
             20                  25                  30 agg tcc agg atg gcc agc ctg ttc cgg tcc tat ctg cca gca atc tgg     144
Arg Ser Arg Met Ala Ser Leu Phe Arg Ser Tyr Leu Pro Ala Ile Trp
         35                  40                  45 ctg ctg ctg agc caa ctc ctt aga gaa agc cta gca gca gag ctg agg     192
Leu Leu Leu Ser Gln Leu Leu Arg Glu Ser Leu Ala Ala Glu Leu Arg
     50                  55                  60
```

```
gga tgt ggt ccc cga ttt gga aaa cac ttg ctg tca tat tgc ccc atg      240
Gly Cys Gly Pro Arg Phe Gly Lys His Leu Leu Ser Tyr Cys Pro Met
 65                  70                  75                  80 cct gag aag aca ttc acc acc acc cca gga ggg tgg ctg ctg gaa tct      288
Pro Glu Lys Thr Phe Thr Thr Thr Pro Gly Gly Trp Leu Leu Glu Ser
                     85                  90                  95 gga cgt ccc aaa gaa atg gtg tca acc tcc aag aac aaa gat gga caa      336
Gly Arg Pro Lys Glu Met Val Ser Thr Ser Lys Asn Lys Asp Gly Gln
                100                 105                 110 gcc tta ggt acg aca tca gaa ttc att cct aat ttg tca cca gag ctg      384
Ala Leu Gly Thr Thr Ser Glu Phe Ile Pro Asn Leu Ser Pro Glu Leu
            115                 120                 125 aag aaa cca ctg tct gaa ggg cag cca tca ttg aag aaa ata ata ctt      432
Lys Lys Pro Leu Ser Glu Gly Gln Pro Ser Leu Lys Lys Ile Ile Leu
        130                 135                 140 tcc cgc aaa aag aga agt gga cgt cac aga ttt gat cca ttc tgt tgt      480
Ser Arg Lys Lys Arg Ser Gly Arg His Arg Phe Asp Pro Phe Cys Cys
145                 150                 155                 160 gaa gta att tgt gac gat gga act tca gtt aaa tta tgt aca tag tag      528
Glu Val Ile Cys Asp Asp Gly Thr Ser Val Lys Leu Cys Thr
                165                 170                 175 agt aat cat gga ctg gac atc tca tcc att ctc ata tgt att ctc aat      576
Ser Asn His Gly Leu Asp Ile Ser Ser Ile Leu Ile Cys Ile Leu Asn
            180                 185                 190 gac aaa ttc act gat gcc caa tta aat gat tgc tgt tta                  615
Asp Lys Phe Thr Asp Ala Gln Leu Asn Asp Cys Cys Leu
        195                 200                 205

<210> SEQ ID NO 2
<211> LENGTH: 139
<212> TYPE: PRT
<213> ORGANISM: Unknown
<220> FEATURE:
<223> OTHER INFORMATION: Description of Unknown Organism:EPIL - Early
      Placenta Insulin-Like Peptide

<400> SEQUENCE: 2

Met Ala Ser Leu Phe Arg Ser Tyr Leu Pro Ala Ile Trp Leu Leu Leu
                 5                  10                  15

Ser Gln Leu Leu Arg Glu Ser Leu Ala Ala Glu Leu Arg Gly Cys Gly
             20                  25                  30

Pro Arg Phe Gly Lys His Leu Leu Ser Tyr Cys Pro Met Pro Glu Lys
         35                  40                  45

Thr Phe Thr Thr Thr Pro Gly Gly Trp Leu Leu Glu Ser Gly Arg Pro
     50                  55                  60

Lys Glu Met Val Ser Thr Ser Lys Asn Lys Asp Gly Gln Ala Leu Gly
 65                  70                  75                  80

Thr Thr Ser Glu Phe Ile Pro Asn Leu Ser Pro Glu Leu Lys Lys Pro
                 85                  90                  95

Leu Ser Glu Gly Gln Pro Ser Leu Lys Lys Ile Ile Leu Ser Arg Lys
            100                 105                 110

Lys Arg Ser Gly Arg His Arg Phe Asp Pro Phe Cys Cys Glu Val Ile
        115                 120                 125

Cys Asp Asp Gly Thr Ser Val Lys Leu Cys Thr
    130                 135

<210> SEQ ID NO 3
<211> LENGTH: 29
<212> TYPE: PRT
```

```
<213> ORGANISM: Unknown
<220> FEATURE:
<223> OTHER INFORMATION: Description of Unknown Organism:EPIL - Early
      Placenta Insulin-Like Peptide

<400> SEQUENCE: 3

Ser Asn His Gly Leu Asp Ile Ser Ser Ile Leu Ile Cys Ile Leu Asn
 1               5                  10                  15

Asp Lys Phe Thr Asp Ala Gln Leu Asn Asp Cys Cys Leu
             20                  25

<210> SEQ ID NO 4
<211> LENGTH: 934
<212> TYPE: DNA
<213> ORGANISM: Unknown
<220> FEATURE:
<223> OTHER INFORMATION: Description of Unknown Organism:EPIL - Early
      Placenta Insulin-Like peptide

<400> SEQUENCE: 4
aggtcagttc tatttttatt tcatctaagc aaaggacatt aaaaattacc attattttag    60
taagcataaa aatagtatta caggaggaaa gttaagaaaa agaagtagaa caaccaaatt   120
caaaacaagc aaagtgcagc agcacattgg gagcaaagag ggatatgaga gtgtgggtag   180
ggcaagtagg gagactaaat aagaactgag ggagaaagtt ccttgtaggt gggtgggaaa   240
ggggtggact dacaccattg acgccaaagc tgagtatagc cctaagccaa ataaatgcct   300
gatgaaggca tgcagaaagc agtctggagc ccagaaggga cacaccagca cagtctggta   360
ggctacagca gcaagtctct aaagaaaggc tgagaacacc cagaacagga gagttcaggt   420
ccaggatggc cagcctgttc cggtcctatc tgccagcaat ctggctgctg ctgagccaac   480
tccttagaga aagcctagca gcagagctga ggggatgtgg tccccgattt ggaaaacact   540
tgctgtcata ttgccccatg cctgagaaga cattcaccac cacccagga gggtggctgc   600 tggaatctgg acgtcccaaa gaatggtgt caacctccaa caacaaagat ggacaagcct   660
taggtacgac atcagaattc attcctaatt tgtcaccaga gctgaagaaa ccactgtctg   720
aagggcagcc atcattgaag aaaataatac tttcccgcaa aaagagaagt ggacgtcaca   780
gatttgatcc attctgttgt gaagtaattt gtgacgatgg aacttcagtt aaattatgta   840
catagtagag taatcatgga ctggacatct catccattct catatgtatt ctcaatgaca   900
aattcactga tgcccaatta aatgattgct gttt                                934

<210> SEQ ID NO 5
<211> LENGTH: 157
<212> TYPE: DNA
<213> ORGANISM: Unknown
<220> FEATURE:
<221> NAME/KEY: CDS
<222> LOCATION: (107)..(157)
<223> OTHER INFORMATION: Description of Unknown Organism:EPIL - Early
      Placenta Insulin-Like peptide

<400> SEQUENCE: 5
cagtctggag cccagaaggg acacaccagc acagtctggt aggctacagc agcaagtctc    60
taaagaaagg ctgagaacac ccagaacagg agagttcagg tccagg atg gcc agc      115
                                               Met Ala Ser
                                                1 ctg ttc cgg tcc tat ctg cca gca atc tgg ctg ctg ctg agc             157
Leu Phe Arg Ser Tyr Leu Pro Ala Ile Trp Leu Leu Leu Ser
     5                  10                  15
```

<210> SEQ ID NO 6
<211> LENGTH: 17
<212> TYPE: PRT
<213> ORGANISM: Unknown
<220> FEATURE:
<223> OTHER INFORMATION: Description of Unknown Organism:EPIL - Early
      Placenta Insulin-Like Peptide

<400> SEQUENCE: 6

Met Ala Ser Leu Phe Arg Ser Tyr Leu Pro Ala Ile Trp Leu Leu Leu
1               5                   10                  15

Ser

<210> SEQ ID NO 7
<211> LENGTH: 123
<212> TYPE: DNA
<213> ORGANISM: Unknown
<220> FEATURE:
<221> NAME/KEY: CDS
<222> LOCATION: (1)..(123)
<223> OTHER INFORMATION: Description of Unknown Organism:EPIL - Early
      Placenta Insulin-Like peptide

<400> SEQUENCE: 7 caa ctc ctt aga gaa agc cta gca gca gag ctg agg gga tgt ggt ccc        48
Gln Leu Leu Arg Glu Ser Leu Ala Ala Glu Leu Arg Gly Cys Gly Pro
1               5                   10                  15 cga ttt gga aaa cac ttg ctg tca tat tgc ccc atg cct gag aag aca        96
Arg Phe Gly Lys His Leu Leu Ser Tyr Cys Pro Met Pro Glu Lys Thr
            20                  25                  30 ttc acc acc acc cca gga ggg tgg ctg                                   123
Phe Thr Thr Thr Pro Gly Gly Trp Leu
        35                  40

<210> SEQ ID NO 8
<211> LENGTH: 41
<212> TYPE: PRT
<213> ORGANISM: Unknown
<220> FEATURE:
<223> OTHER INFORMATION: Description of Unknown Organism:EPIL - Early
      Placenta Insulin-Like Peptide

<400> SEQUENCE: 8

Gln Leu Leu Arg Glu Ser Leu Ala Ala Glu Leu Arg Gly Cys Gly Pro
1               5                   10                  15

Arg Phe Gly Lys His Leu Leu Ser Tyr Cys Pro Met Pro Glu Lys Thr
            20                  25                  30

Phe Thr Thr Thr Pro Gly Gly Trp Leu
        35                  40

<210> SEQ ID NO 9
<211> LENGTH: 153
<212> TYPE: DNA
<213> ORGANISM: Unknown
<220> FEATURE:
<221> NAME/KEY: CDS
<222> LOCATION: (1)..(153)
<223> OTHER INFORMATION: Description of Unknown Organism:EPIL - Early
      Placenta Insulin-Like peptide

<400> SEQUENCE: 9 ctg gaa tct gga cgt ccc aaa gaa atg gtg tca acc tcc aac aac aaa        48
Leu Glu Ser Gly Arg Pro Lys Glu Met Val Ser Thr Ser Asn Asn Lys
1               5                   10                  15 gat gga caa gcc tta ggt acg aca tca gaa ttc att cct aat ttg tca        96

```
Asp Gly Gln Ala Leu Gly Thr Thr Ser Glu Phe Ile Pro Asn Leu Ser
            20                  25                  30 cca gag ctg aag aaa cca ctg tct gaa ggg cag cca tca ttg aag aaa        144
Pro Glu Leu Lys Lys Pro Leu Ser Glu Gly Gln Pro Ser Leu Lys Lys
        35                  40                  45 ata ata ctt                                                            153
Ile Ile Leu
    50
```

<210> SEQ ID NO 10
<211> LENGTH: 51
<212> TYPE: PRT
<213> ORGANISM: Unknown
<220> FEATURE:
<223> OTHER INFORMATION: Description of Unknown Organism:EPIL - Early
    Placenta Insulin-Like Peptide

<400> SEQUENCE: 10

```
Leu Glu Ser Gly Arg Pro Lys Glu Met Val Ser Thr Ser Asn Asn Lys
 1               5                  10                  15

Asp Gly Gln Ala Leu Gly Thr Thr Ser Glu Phe Ile Pro Asn Leu Ser
            20                  25                  30

Pro Glu Leu Lys Lys Pro Leu Ser Glu Gly Gln Pro Ser Leu Lys Lys
        35                  40                  45

Ile Ile Leu
    50
```

<210> SEQ ID NO 11
<211> LENGTH: 93
<212> TYPE: DNA
<213> ORGANISM: Unknown
<220> FEATURE:
<221> NAME/KEY: CDS
<222> LOCATION: (1)..(93)
<223> OTHER INFORMATION: Description of Unknown Organism:EPIL - Early
    Placenta Insulin-Like peptide

<400> SEQUENCE: 11

```
tcc cgc aaa aag aga agt gga cgt cac aga ttt gat cca ttc tgt tgt         48
Ser Arg Lys Lys Arg Ser Gly Arg His Arg Phe Asp Pro Phe Cys Cys
 1               5                  10                  15 gaa gta att tgt gac gat gga act tca gtt aaa tta tgt aca tag             93
Glu Val Ile Cys Asp Asp Gly Thr Ser Val Lys Leu Cys Thr
            20                  25                  30
```

<210> SEQ ID NO 12
<211> LENGTH: 30
<212> TYPE: PRT
<213> ORGANISM: Unknown
<220> FEATURE:
<223> OTHER INFORMATION: Description of Unknown Organism:EPIL - Early
    Placenta Insulin-Like Peptide

<400> SEQUENCE: 12

```
Ser Arg Lys Lys Arg Ser Gly Arg His Arg Phe Asp Pro Phe Cys Cys
 1               5                  10                  15

Glu Val Ile Cys Asp Asp Gly Thr Ser Val Lys Leu Cys Thr
            20                  25                  30
```

<210> SEQ ID NO 13
<211> LENGTH: 48
<212> TYPE: DNA
<213> ORGANISM: Unknown
<220> FEATURE:
<223> OTHER INFORMATION: Description of Unknown Organism:EPIL - Early -continued

```
          Placenta Insulin-Like peptide

<400> SEQUENCE: 13
gtgagagccc tggactacca aacaatcaga atgagggctg aaaaaaca                48

<210> SEQ ID NO 14
<211> LENGTH: 47
<212> TYPE: DNA
<213> ORGANISM: Unknown
<220> FEATURE:
<223> OTHER INFORMATION: Description of Unknown Organism:EPIL - Early
      Placenta Insulin-Like peptide

<400> SEQUENCE: 14
acatgaatgt ttttcctcac ctttcattcc tctctttac ttcacag                 47

<210> SEQ ID NO 15
<211> LENGTH: 35
<212> TYPE: DNA
<213> ORGANISM: Unknown
<220> FEATURE:
<223> OTHER INFORMATION: Description of Unknown Organism:EPIL - Early
      Placenta Insulin-Like peptide

<400> SEQUENCE: 15
gactcgagtc gacatcgatt tttttttttt ttttt                              35

<210> SEQ ID NO 16
<211> LENGTH: 35
<212> TYPE: DNA
<213> ORGANISM: Unknown
<220> FEATURE:
<223> OTHER INFORMATION: Description of Unknown Organism:EPIL - Early
      Placenta Insulin-Like peptide

<400> SEQUENCE: 16
gcatcggcgc ggccgcggag gcccccccccc ccccc                             35
```

PROTEIN CALLED EPIL/PLACENTIN, PROCESS FOR THE PREPARATION OF THIS PROTEIN AND PHARMACEUTICAL COMPOSITION CONTAINING SUCH, DNA CODING FOR SAID PROTEIN

This application is a divisional of Ser. No. 08/482,842, filed Jun. 7, 1995, now U.S. Pat. No. 5,910,480.

The present invention concerns a new protein called placentin or EPIL, its analogs, the procedures for their preparation and their applications.

Insulin, IGF1, IGF2 and relaxin belong to a family of peptide hormones having certain common structures and functions, particularly their influence upon cell proliferation, development, differentiation and metabolism.

Insulin is well known as being an endocrine pancreatic hormone regulating energy metabolism. Growth factors of insulin-IGF-1 type are growth promoting peptides involved in endocrine, paracrine and autocrine regulation of cell growth and which are expressed in numerous Tissues. IGF2 has similar properties but is expressed in higher quantities during the prenatal period and is considered as being a fetal growth factor.

Relaxin induces remodeling of connective tissue in the reproductive tract and inhibits uterine contractions. Its functional role in the brain, where extensive expression has been obtained, remains to be elucidated.

Recently, Ley-I-Ls were added to this family which are currently cloned in cDNA form and whose biological activity remains to be determined. This peptide family commonly presents structural characteristics defined by the position of different cysteines essential for the formation of a tertiary structure.

Insulin, which is the prototype for this family, comprises two peptide A and B chains connected by disulfide bridges. It is coded by a mRNA which is translated into preproinsulin. The peptide signal, like the connecting C peptide, are excised by post-translational modification; this also applies to relaxin although the IGFs are matured differently without elimination of the C peptide and remain as a single chain. It has been shown that all the members of this family attach themselves to cell surface receptors. These receptors have been identified by molecular cloning and characterized in detail for insulin and IGF. They belong to the superfamily of tyrosine protein kinase receptors (Tyr-PK receptors) which comprises growth factor receptors and their oncogene analogs such as c-neu/erb-B-2 (EGF receptor), c-met (hepatocyte growth factor receptor), fms (CSF-1 receptor) and trk (NGF receptor).

The transduction route of the intracellular signal for these receptors is characterized by tyrosine-kinase activity which produces autophosphorylation of the tyrosine residues on the receptor followed by a chain of events corresponding to phosphorylations. This includes, in particular, the activation of IRS-1 (particularly for insulin and IGF), P13K, Shc, GBRZ, Sos, Ras, Raf and the kinase mitogenesis activating protein (MAP) especially when the cascade of phosphorylation affects different cell processes such as transcription.

The pleiotropic physiological effects of this cascade of signals are generally the subject of intense research.

BRIEF DESCRIPTION OF THE DRAWINGS

FIGS. 1A and 1B depict a DNA sequence and corresponding amino acid sequence for EPIL/placentin.

FIGS. 2A and 2B depict the detailed structure of EPIL/placentin including the signal sequence (position −17 to −1), the B chain (position 1 to 41), the C peptide (position 42–92), and the A chain (position 93–122).

The present invention concerns, more particularly, a new molecule of this insulin family which is called hereinafter placentin or EPIL (Early Placenta Insulin-Like peptide) whose amino acid sequence and the DNA sequence which codes for this protein corresponds to the ID 1 sequence.

EPIL/Placentin was isolated from a cDNA bank of cytotrophoblastic cells prepared from placenta taken during the first trimester of pregnancy. Northern blot analysis (performed on very wide sampling of normal tissues) revealed detectable RNA levels only in placental tissue.

The amino acid sequence obtained shows an arrangement of cysteine residues for protein according to the invention that is characteristic of the insulin family.

The treatment of target cells with media fed with cell cultures expressing the recombinant protein seems to induce a pattern of tyrosine phosphorylation similar to that observed after treatment with insulin.

Finally, EPIL/placentin induces DNA synthesis.

This is why the present invention concerns, more particularly, a protein called EPIL/placentin, a protein with a formula corresponding to sequence ID 1, also represented in FIG. 1, and its analogs showing placentin-type activity and obtained by deletion and/or substitution.

On sequence ID 1, the structure of EPIL/placentin corresponds to the amino acid structure following methionine at position 36 as far as the amino acid at position 174.

The references to the DNA sequences of EPIL/placentin correspond to this sequence.

The nucleic sequences existing before the first presumed ATG (underlined) and after the stop codon are in small letters.

EPIL/Placentin analogs are proteins or peptides which have high ammo acid homology, particularly over 60% homology, preferably 80% with the compound corresponding to sequence ID 1, which could be obtained by deletion or by substitution while preserving the essential characteristics of EPIL/placentin. These analogs shall sometimes be called "EPIL/placentin-type compounds".

In particular, the present invention concerns fragments which show certain epitopes characteristic of EPIL/placentin activity, in particular EPIL/placentin-type proteins which have at least the first 20 amino acids of the N-terminal extremity of sequence ID 1.

The present invention evidently concerns EPIL/placentin or its analogs in glycosylated or non-glyosylated form and the proteins with or without the disulfide bridges of the original protein. Indeed, this protein may be prepared by extraction using biological samples but shall be preferably obtained via techniques using generic engineering and its secondary structures may vary in accordance with the host organism.

The invention also concerns a molecule chosen among:
(a) the DNA sequence of the ID 1 sequence,
(b) DNA sequences likely to hybridize to the preceding sequence and which code for a EPIL/placentin-type polypeptide, and
(c) DNA sequences which taking into account the genetic code correspond to sequences (a) or (b) and which code for a EPIL/placentin-type polypeptide.

In particular, the invention concerns the DNA sequence corresponding to sequence ID 1.

Evidently, the DNA sequences previously mentioned may be genomic or genomic-type sequences, that is to say that certain elements may be separated by introns which will be excised to lead to the expression of mature EPIL/placentin.

The preceding DNA sequences may be incorporated into cloning or expression vectors of EPIL/placentin or its analogs, preferably under the control of elements assuring their expression in a defined host cell.

The systems of expression in prokaryotic or eucaryotic cells are well known to men of the art. These may in particular concern systems of plasmid type or viral type comprising promoters assuring expression in the host cell and also provided with the necessary terminal elements.

But they may also concern integration vectors which may comprise their own system of expression or else be designed to integrate into the chromosomes in places where they come under the promotion of a chromosome promotor, in particular in the case of prokaryotic cells, using the homologous recombination technique.

The present invention also concerns host cells characterized in that they comprise a self-replicating vector expressing EPIL/placentin or a EPIL/placentin analog in accordance with the invention or a DNA sequence in accordance with the invention incorporated into a chromosome and expressing EPIL/placentin or a EPIL/placentin analog.

As previously indicated, these may be eukaryotic cells, in particular mammalian cells of CHO cell type, or cultured cells of other types more appropriate to the preparation of EPIL/placentin in its mature form; but it is also possible to contemplate using bacterial cells for example: in this case it may be appropriate to subject the protein obtained to additional modifications.

These techniques are again known to men of the art and shall not be described more fully, except within the context of certain examples below.

The cells thus transformed by a self-replicating vector expressing the protein or having integrated the sequence expressing the protein in its chromosomes may be used by culture in a process permitting the preparation of EPIL/placentin or its analogs.

This particularly concerns a process for the preparation of EPIL/placentin or its analogs characterized by the culturing of cells from which EPIL/placentin or its analogs shall be extracted either directly or from the culture medium.

EPIL/Placentin may in particular be extracted by inmuno-purification.

The present invention also concerns recombination products obtained through the previously performed process.

In certain cases, the protein may be prepared in fused form, in particular when a peptide-type analog of EPIL/placentin is involved, or when fusion with this protein provides easier access to the action site of EPIL/placentin or its analogs, or when, in certain cases, this protein can be used to deceive certain natural systems by giving the protein of interest longer life.

Finally, the present invention relates to pharmaceutical compositions using EPIL/placentin or its analogs as an active ingredient.

As indicated, EPIL/placentin has multiple activities, in particular it may, like other type 1 human growth factors, offer cardiac-related activity, in particular for the treatment and prevention of certain heart disorders such as acute cardiac failure.

This protein or some of its analogs may offer growth factor and lactation type activity. Also, the products may be used in the regeneration process of nerve, muscle, skin or bone tissues, especially in degenerative or endocrine pathologies, traumatic lesions or viral illnesses.

Finally, EPIL/placentin or its analogs may offer action in connection with the control of all phenomena relating to conception in man or animal.

The present invention also concerns antibodies and more particularly specific monoclonal antibodies of EPIL/placentin or its analogs, and an in vitro diagnosis method which uses EPIL/placentin or its analogs and/or corresponding antibodies to detect abnormal levels of EPIL/placentin in samples that may or may not be physiological.

DNA fragments corresponding to the previously mentioned sequences may be integrated into "sense" or "anti-sense" treatment strategy; EPIL/placentin or its analogs could be integrated into a strategy targeting certain pharmaceutically active molecules towards receptors of EPIL/placentin or its analogs.

The detailed structure of EPIL/placentin called EPIL corresponds to sequence of FIG. 2 [SEQ ID NOS.: 4–14] that is to say a peptide signal at position −17 to −1 [SEQ ID NOS.: 5 & 6], a B chain 1 to 41 [SEQ ID NOS.: 7 & 8], a connecting C peptide from 42 to 92 [SEQ ID NOS.: 9 & 10] then an A chain from 93 to 122 [SEQ ID NOS.: 11 & 12].

This structure relates EPIL to proinsulin or prorelaxin.

In particular, the position of the disulfide bridges must lead to an insulin-type three-dimensional structure.

Other characteristics and advantages of the present invention will appear on reading the following examples making reference to sequences ID 1 and FIG. 2 [SEQ ID NOS.: 4–14] corresponding to the sequence of EPIL/placentin and of the human gene coding for this protein.

EXAMPLES

The identification of EPIL/placentin is the outcome of specific research seeking to determine the molecules involved in cell growth and/or in neoplasic processes.

Although placenta is a normal tissue, its constituting cells have numerous properties in common with neoplasic cells, in particular with invasive, highly mitotic cytotrophoblasts which may penetrate the maternal tissue. These trophoblasts are an inexhaustible source of growth factors, hormones and growth factor receptors in particular.

Current studies show that the genes preferably expressed in trophoblastic cells may also be preferably expressed in neoplasic cells.

However taking into account that placenta, and in particular trophoblasts, remain under full control during normal pregnancy, the trophoblastic molecules corresponding to this control are highly interesting candidates as anticancerous agents or likely to control the cancerisation process.

This is why the isolation method used is a cDNA subtraction method having recourse to PCR technology on young trophoblasts. This permitted the detection of genes which are overexpressed in these cells and which may play a role in cellular growth and regulation.

Material and Methods

Tissues

Placentas of 5 to 12 weeks, full term placentas and surgical samples of normal and tumorous tissues were refrigerated immediately (within 10 minutes after surgery) and preserved in liquid nitrogen until RNA preparation. These tissue collections were obtained and used in accordance with protocols approved by the Committees of the different hospitals.

Cells

The human cell lines used throughout this study and their histological origins are as follows: gestational choriocarcinoma (JAr and JFG-3); hepatocellular carcinoma (PLC/PRF/5 and Hep G2); colon adenocarcinoma (LSI80); ovarian carcinoma (OVI/p, OVIVCR), the OVI/VCR cell line is derived from OVI/p and is resistant to vincristin; epidermoid carcinoma (A431); lung carcinoma (A427); epithelioid carcinoma of the cervix (HeLa); mammary carcinoma (McF7, MDA-MB-361, SK-BRA-3, BTu-20 and BTu-474); mammary cells transformed by SV-40 (HBL-100): neuroblastoma cell line (SHSY-5Y); normal fibroblast cell line (CCL-137).

All these cell lines being available to ATCC with the exception of IGR/OVI (OVI/p) and OVI/VCR.

These cell lines are cultured in a DMEM or RPMI-1460 medium (Gibco-BRL Laboratories, Gaithersburg, Mass.) supplemented with 10% fetal calf serum inactivated by heat, 10 μm non essential amino acids, 4 mM glutamin, 100 U/ml penicillin and 100 μg/ml streptomycin at 37° C. with 5% CO2.

Isolation of the Cyrotrophoblasts

The cytotrophoblasts are purified as described by Kliman et al. Endocrinology, 118: 1567–1582, 1986. Briefly, the villi tissue of first trimester placenta are dispersed with trpysin and deoxyribonuclease-1. The dispersed cells are then purified through a 5–70% Percoll gradient (Pharmacia). The 1040–1060 g/ml density band is collected. Microscropic examination shows that it comprises cytotrophoblastic cells with less than 5% contamination with non-trophoblastic cells such as macrophages, fibroblasts and endorehlial cells.

Preparation of RNA

Total RNA is prepared from preconfluent cell cultures or refrigerated tissues using guanidinine isothiocyanate and ultracentrifugation on a cesium chloride gradient by adapting the protocol described by Chirgwin et al. The polysome RNAs associated with the endoplasmic reticulum membranes (MB-RNA) are purified as described previously. After trypsination and purification through a Percoll gradient, the cytotrophoblastic cells art homogenized, then the MB-RNAs are isolated on a sucrose gradient to which is added a vanadyl ribonucleoside complex as ribonuclease inhibitor.

cDNA Synthesis and PCR Amplification 0.1 μg MB-RNA are dissolved in 5 μl DEPC treated water and denatured with 0.1 M MeHgOH and β-mercaptoethanol. The first cDNA strand is synthesized with the reverse transcriptase of avian myoblastosis virus (Invitrogen kit, San Diego) using the modified dT primer indicated below (Frohman et al. Proc. Natl. Acad. Sci. U.S.A., 85: 8998–9002, 1988). The RNA-cDNA heteroduplexes of size ranging from 0.5 to 2 kb are electroeluted after migration in 2% agarose gel. A dG oligo tail is added to the 3' end of the first cDNA strand with the terminal deoxynucleotide transferase and the RNA is eliminated by alkaline hydrolysis. The cDNAs are amplified with non specific primers including restriction sites for Notl and Sall enzymes.

The sequence [SEQ ID NO.: 15] of the T primer used for reverse transcription and PCR is as follows:

5'-GACTCGAGTCGACATCGATTTTTTTTTTTTTTTTT-3'

The C primer [SEQ ID NO.: 16] is identical to that described by Loh et al., (Science, 243: 217–220, 1989):

5'GCATCGGCGCGGCCGCGGAGGCCCCCCCCCCCCCC-3'

The reaction mixture comprises 1.25 mM of each of the 4 triphosphate desoxyribonucleotides, 0.5 μM of each primer and 2.5 units of Taq polymerase in 50 mM Kcl-10 mM Tris-HCl (pH 8.3)—3.5 mM MgCl2–0.01% gelatin. Amplification is carried out in a thermal cycler for 25 cycles of 20 seconds at 94° C., 30 seconds at 55° C. and 1 minute at 72° C. The products are loaded on 1% agarose gel at low fusion. The 0.5–2 kb region is then excised and reamplified under the same conditions. The products are precipitated, fully digested with Notl and Sall, the sizes are selected as previously and electroeluted from agarose, precipitated and quantified.

The total cDNA of full term placenta and T lymphocytes activated with phyrohemagglutinin and cultivated for several days in the presence of IL2 was prepared using a double strand cDNA synthesis method.

Construction of the Subtracted cDNA Bank

Subtraction hybridization is performed as described by Klickstein (Klickstein et al. Current protocols in molecular biology, pp 5.8.9.–5.8.15 Wiley Interscience, 1989). 0.2 μg cDNA from cytotrophoblastic cells amplified by PCR are left to digest with Notl and Sall, mixed with 8 μg cDNA of activated T lymphocytes and 8 μg cDNA of full term placenta digested with Alul and Rsal, dissolved in 40 μl hybridization buffer (50% deionized formamide; 10 mM sodium phosphate buffer, pH 7; 5×SSC, 0.1% SDS; 10 mM EDTA), denatured for 5 minutes at 98° C. and incubated for 24 hours at 37° C.

The sequences common to target and competitor are collected to form duplexes between the short fragments (Alu/Rsa, competitor) and the long fragments (Not/Sal of the target) by inhibiting the formation of cohesive ends. Complementary cDNA strands specifically expressed in the young cytotrophoblasts permit the regeneration of the Notl and Sall cohesive ends for unidirectional cloning in the pBSKII sites+vector phagemid (Stratagene).

Bank Sifting

The subtracted cDNA bank is spread over a gelose culture medium and the recombinant colonies are collected and cultured in the LB medium then amplified by PCR. The plasmid DNAs, prepared by the boiled minipreparation method (Del Sal G. et al. Nucleic Acids Res., 16: 9878, 1988) and digested with Notl and Sall or the insert products amplified by PCR using the original primers, are analyzed by Southern blotting on 1.2% agarose gels. The average size of inserts is between 500 and 1000 nucleotides. The gels are transferred in duplicate onto nylon membranes (Hybond N, Amersham) in an alkaline buffer. The probes used for hybridization are total cDNAs synthesized from young placentas, full term placentas and activated T lymphocytes 32P-labeled (Amersham) by random multiple priming. Hybridization is carried out for 18 hours at 42° C. followed by stringent washing in 0.1×SSC at 50° C. and autoradiography.

Northern Blot Analysis

5 μg of total RNA taken from different tissues and cell lines are analyzed on 1% agarose gel containing 2.2 M of formaldehyde. On completion of electrophoresis, the gel is rinsed with bi-distilled water and treated with 10×SSC for 30 minutes. The RNA is then transferred to a reinforced nitrocellulose membrane (Schleicher & Schuell, Dassel) in the 20×SSC transfer buffer for 18 hours. The transferred RNAs are fixed to the membranes by UV radiation before hybridization. The probes used to hybridize the membranes are excised inserts 32P-labeled by random multiple priming, or single strand probes generated by PCR using a universal antisense primer. Hybridization is carried out overnight at 42° C. followed by stringent washing in 0.1×SSC at 50° C. and autoradiography.

DNA Sequencing and Analysis

The plasmid DNAs are prepared using the boiled minipreparation method. DNA sequencing is performed with the Sequenase kit, version 2.0 (U.S. Biochemical). The primers are either universal M13, T3, or T7 primers or specific internal primers. Reaction products are analyzed on gels containing 6% acrylamide and 50% urea. The sequences obtained are compared with the sequences of the different data banks.

Analysis

The clones which do not give any hybridization signal with standardized probes are analyzed by partial sequencing and comparison with these data banks.

One of the clones corresponding to EPIL/placentin corresponds to the amino acid sequence corresponding to sequence ID 1.

Total RNA and polyA samples prepared from normal or transformed cell lines and from corresponding tissues are subjected to Northern blotting with labeled, single strand, antisense EPIL/placentin cDNA probes. Hybridization signals are detected solely in the placentas, especially early pregnancy placentas and are practically non-existent in the other tissues as shown in the table given below (Table 1):

TABLE 1

| YOUNG PLACENTA | ++++ |
|---|---|
| FULL TERM PLACENTA | ++ |
| NORMAL LIVER | – |
| TUMOROUS LIVER | – |
| NORMAL BLADDER | – |
| TUMOROUS BLADDER | – |
| NORMAL OMENTUM | – |
| TUMOROUS OMENTUM | – |
| NORMAL ESOPHAGUS | – |
| TUMOROUS ESOPHAGUS | – |
| NORMAL COLON | – |
| TUMOROUS COLON | – |
| NORMAL STOMACH | – |
| NORMAL CERVIX UTERI | – |
| NORMAL ENDOMETRIUM | – |
| NORMAL OVARY | – |
| TUMOROUS BREAST | – |
| TUMOROUS GANGLION | – |
| NORMAL SPLEEN | – |
| NORMAL RECTUM | – |

TABLE 1-continued

| TUMOROUS RECTUM | – |
|---|---|
| NORMAL FALLOPIAN TUBE | – |
| NORMAL SKIN | – |
| NORMAL MYOMETRIUM | – |
| NORMAL ADRENAL GLAND | – |
| NORMAL THYROID | – |
| TUMOROUS THYROID | – |

Studies carried out on murine and simian products show analogies indicating significant functional similarities between species.

EPIL/Placentin Expression

For the eukaryotic expression of EPIL/placentin, cDNA was inserted into the pEK-CMV expression vector in the sense and antisense position.

Two cell types were used to examine the possible effects of post-translational modifications inherent to cell types. COS-7 monkey kidney cells were transfected by DEAE for transient expression while the human trophoblastic cells transformed by SV40 (3AsubE) were transfected by CaPO4 for stable, transient expression.

The COS-7 and 3AsubE cells do not express any detectable level of EPIL/placentin mRNA with northern blot. The transfected cells are fed with serum-free culture medium The media fed with sense or antisense transfected cells are analyzed to detect the presence of recombinant proteins.

The biological activity of the recombinant protein is analyzed on different target cells considering that the specific receptors may exist or that the protein may attach itself to other receptors for molecules of proximal structure as was observed for insulin and IGF.

Preliminary results suggest that EPIL/placentin would induce tyrosine phosphorylation of cellular proteins and would have biological activity on trophoblastic cells growth.

What is claimed is:

1. An isolated DNA molecule comprising a DNA sequence which encodes EPIL/placentin protein having sequence ID 2 or analogs thereof having EPIL/Placentin-type action and obtained by deletion and/or substitution.

2. An isolated DNA molecule comprising the nucleotide sequence of sequence ID 1.

3. An expression vector for the expression of EPIL/placentin or analogs thereof having EPIL/placentin-type action, said vector comprising a DNA sequence encoding EPIL/placentin having sequence ID 2 or a DNA sequence encoding analogs thereof obtained by deletion and/or substitution.

4. A host cell comprising the expression vector of claim 3.

5. The host cell according to claim 4, wherein said host cell is a eukaryotic cell.

6. The host cell according to claim 4, wherein said host cell is a bacterium.

7. A process for the preparation of EPIL/placentin or analogs thereof having EPIL/placentin-type action, said process comprising the steps of (a) culturing a host cell according to claim 4; and (b) extracting EPIL/placentin or analogs thereof directly from the host cells.

8. A process for the preparation of EPIL/placentin or analogs thereof having EPIL/placentin-type action, said process comprising the steps of (a) culturing a host cell according to claim 4; and (b) extracting EPIL/placentin or analogs thereof from the culture medium.

* * * * *